United States Patent
Madray

(10) Patent No.: US 6,231,830 B1
(45) Date of Patent: May 15, 2001

(54) METHOD OF MAKING MOLECULAR CHLORINE DIOXIDE

(76) Inventor: George Madray, 4 Carteret Rd., Brunswick, GA (US) 31525

( * ) Notice: Subject to any disclaimer, the term of this patent is extended or adjusted under 35 U.S.C. 154(b) by 0 days.

(21) Appl. No.: 09/262,618

(22) Filed: Mar. 4, 1999

(51) Int. Cl.⁷ .................................................. C01B 11/02
(52) U.S. Cl. .................................. 423/477; 252/187.21
(58) Field of Search .................. 423/477; 252/187.21, 252/187.23

(56) References Cited

U.S. PATENT DOCUMENTS

| | | | |
|---|---|---|---|
| 3,271,242 | * | 9/1966 | McNicholas ............................ 424/65 |
| 4,113,857 | * | 9/1978 | Shetty ................................ 424/78.25 |
| 5,342,601 | * | 8/1994 | Cawlfield et al. .................... 423/478 |
| 5,405,549 | * | 4/1995 | Pitochelli ............................. 422/477 |

OTHER PUBLICATIONS

Masschelein "Chlorine Dioxide, Chemistry & Environmental Impact of Oxychlorine Compounds", pp. 90–93, 1979 (No Month).*

Jacobson, "Encyclopedia of Chemical Reactions", vol. II, p. 726, 1948 (No Month).*

* cited by examiner

Primary Examiner—Ngoc-Yen Nguyen

(57) ABSTRACT

A method for manufacturing molecular chlorine dioxide, by the addition of potassium iodide to a solution of alkali metal chlorite. The metal chlorite and the potassium iodide are kept separate, until the need for the generation of chlorine dioxide arises—to ensure long-shelf life. After initiation or activation of the chlorite anion to form chlorine dioxide, the beneficial properties of chlorine dioxide can be used, for different health and cosmetic purposes. Such uses include the treatment of herpes, dandruff, acne, skin rashes (e.g. poison ivy), ulcers, bed sores, warts, nail fungus, athletes foot, sun burn and gum disease; and as an antiseptic, disinfectant, and general deodorant form refrigerator sprays to oral mouthrinses.

11 Claims, No Drawings

METHOD OF MAKING MOLECULAR CHLORINE DIOXIDE

FIELD OF INVENTION

The invention relates to a broad field, being as broad as are the properties of chlorine dioxide. For example, in the field of dentistry alone, it can be used as a biofilm control to prevent the buildup of plaque which is responsible for tooth decay, as a whitener maintenance, as an oral/periodontal irrigant and as a breath freshener.

DESCRIPTION OF THE PRIOR ART

Chlorine dioxide ($ClO_2$) has many beneficial properties. Chlorine dioxide is an efficient oxidant. Because it readily reacts with substances (phenolics and sulfides) known to cause taste and odor problems, chlorine dioxide is a widely used treatment for drinking water. Chlorine dioxide has other beneficial properties resulting from its ability to maintain its oxidizing power and antimicrobial properties over a wide pH range. For example, chlorine dioxide is effective against viruses, bacteria, and protozoan cysts. Chlorine dioxide has been shown to be effective in controlling cryptosporidium (Peters, J.; Mazas, E.; Masschelein, W.; 1989, "Effect of Disinfection of Drinking water with Ozone or Chlorine Dioxide on Survival of Cryptosporidium parvum Oocyst". Appl. Environ. Microbiol., 55(6): 1519–1522); (Korich, D.; Mead, J.; Madore, M.; Sinclair, N.; Sterling. C. 1990, "Effects of Ozone, Chlorine Dixoide, Chlorine and Monochloramine of Cryptosporidium parvum Oocyst Viability". Appl. Environ. Microbiol., 56:1423–1428.);(Finch, G.; Liyanage, L.; Belosivic, M. 1995, "Effect of Chlorine Dioxide on Cryptosporidium and Giardia. In Proc. 3rd International Symposium on Chlorine Dioxide Use in Drinking Water, Wastewater and Industrial Applications. CMA, USEPA, and AWWARF.) which causes severe gastrointestinal problems (and even death) in AIDS and immunocompromised individuals. In contrast, chlorine is not effective in treating water sources containing cryptosporidium.

Other applications include its use as a bleaching agent, disinfectant, deodorant, and biofilm control. Even though it is not well understood, microbial cell walls and microbial membranes, being different from human cells, rupture when $ClO_2$ penetrates them at concentrations even below one part per million (PPM) whick is equivalent to one milligram per liter (mg/L). Alteration of electrolytic permeability, and metabolic processes quickly follow, destroying the microbes of which no immunity results.

Studies have been undertaken to determine if different oxychlorine species result in significant genetic or carcinogenic hazards to humans. Meier et al. studied the effect of subchronic and acute oral administration of chlorine, chlorine dioxide, sodium chlorite and sodium chlorate on the induction of chromosomal aberrations and spermhead abnormalities in mice (Environ. Sci. Technol., 28,592 (1994). Only the highly reactive hypochlorite ion (chlorine) resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine (Proc. AWWA Disinfect. Semin., 24 pp (1977); Chem. Abs. 93,173513f.). This observation has more recently been confirmed by Richardson et al in an extensive study of the reaction of chlorine dioxide with water borne organics by the EPA (Environ. Sci. Technol., 28, 592 (1994)).

Two subchronic 90-day animal toxicity studies have been reported (Chemical Manufacturers Association (CMA). 1992, "Study Report of a 90 Day Feeding Study for Sodium Chlorite in the Rat". Arlington Va.);(Harrington, R.; Romano, R.; Gates, D.; Ridgeway, P. 1995, "Subchronic Toxicity of Sodium Chlorite in the Rat". Jour. Amer. Coll. Toxicol., 14(1):21–33) for sodium chlorite. The general toxicological findings include: acute oral $LD_{50}$=150 mg/kg, chronic no effect level=7.4 mg/kg, chronic mild effect level= 19 mg/kg. Based on these data, a normal use pattern of a mouthrinse product (5,000 mg/L $NaCLO_2$ concentration, 3×per day, 90% expectoration) for a 150 1b person maintains a >150 fold safety margin for acute toxicity effects. If the same person were to completely swallow the mouthrinse, a >20 fold safety margin is still maintained.

Richter, according to U.S. Pat. No. 5,738,840 uses hypochlorite to produce chlorine dioxide by using a molar ratio of metal hypochlorite salt to chlorite salt of up to 10:1. But, the stoichiometry of the reation of sodium chlorite with sodium hypochlorite to produce chlorine dioxide predicts that 2 moles of chlorite ion are required to react with 1 mole of hypochlorite ion to generate 2 moles of chlorine dioxide:

$$2NaCLO_2 + NaOCL + H_2O \rightarrow 2ClO_2 + 2NaOH + NaCL$$

This means that under ideal conditions without the possibility of side reactions, a 2:1 molar ratio of sodium chlorite to sodium hypochlorite will produce 2 moles of chlorine dioxide. However, solutions of sodium hypochlorite can decompose over time (Adam, L; Bubnis, B.; Gordon, G. "Minimizing Chlorate Ion Formation in Drinking Water When Hypochlorite Ion Is the Chlorinating Agent", American Water Works Association—Research Foundation (AWWA-RF ISBN 0-89867-781-5) Denver Colo., 1994, 195pp.). Thus, one purpose for maintaining an excess hypochlorite ion concentration is to ensure that the concentration of hypochlorite ion exceeds the minimum stoichiometric required after 9 months storage. A drawback to this embodiment is that when the hypochlorite ion concentration is in large excess, the resulting solution after mixing can have as much as 2,000 times more hypochlorite ion (chlorine) than chlorine dioxide (details are in next paragraph). It is well documented that chlorine disinfection is potentially accompanied by unwanted side reactions leading to the formation of trihalomethanes and possible long-term health risk. Decomposition of hypochlorite ion can also result in a build-up of chlorate ion, an unwanted by-product.

$$3OCl^- \rightarrow ClO_3^- + 2Cl^-$$

So, the reason for Richter's higher molar ratio is because the half-life of NaOCl is approximately 30 days. In order to have a product on a retail shelf for a period of 6–9 months, with its separate activator vial, this higher molar ratio is necessary. This excess hypochlorite ion means that initially, when the hypochlorite ion is fresh, there is more hypochlorite ion than generated chlorine dioxide. Using a 0.2% (2000 mg/L) solution of sodium chlorite with 10 times as much sodium hypochlorite or 2% (20,000 mg/L), and generating approximately 10 mg/L of chlorine dioxide, one will have 2,000 times more hypochlorite ion than chlorine dioxide. This makes Richter's product a chlorinator, rather than an oxygenator (if his product is used soon after its formulation), with resulting trihalomethanes, mentioned above as a suspect health risk. Another disadvantage of the Richter patent, is that after the 9th month, when sodium hypochlorite levels are in the 5–40 mg/L range it infringes the Oikawa et al., patent. A further disadvantage, is that after 12 months when hypochlorite ion levels are nil to non-existent, no activation occurs at all.

Oikawa et al., U.S. Pat. No. 5,165,910 uses hypochlorite ion to produce chlorine dioxide. They discovered that much less hypochlorite ion than a molar ratio of 1:2 of hypochlorite to sodium chlorite is all that is necessary to produce from 15–30 mg/L from sodium chlorite concentrations up to 20,000 mg/L. They state, as well noted among those skilled in the art, that chlorine dioxide can be a deodorizer. This would include using $ClO_2$ on substrates from refrigerators to oral cavities, which raises genuine concerns about the validity of the Richter patent, which is used in oral cavities.

Ratcliff, U.S. patents e.g. U.S. Pat. Nos. 4,689,215; 4,696,811; 4,837,009, and McNicholas et al., U.S. Pat. No. 3,271,242 use a deodorizing oral rinse of approximately 1.25–<2.0 mg/L $ClO_2$. Theses patents, although they generate some $ClO_2$, would clearly be better served by having higher concentrations of molecular chlorine dioxide. This is because it is well known that the deodorizing action comes from the small amount of $ClO_2$ which is present in their "stabilized chlorine dioxide" (primarily a sodium chlorite solution). Even though it is obvious that greater concentrations of $ClO_2$ would give a deodorizing mouthwash greater efficiency, the Ratcliff and Nicholas patents can not achieve this. This is because their sodium chlorite solution has no separate activator to produce the $ClO_2$. The advantage they have over the Richter patent is that the shelf life can be 2+years.

BACKGROUND OF THE INVENTION

The term "stabilized chlorine dioxide" (Kick-Othmer Encyclopedia of Chemical Technology, Forth Ed., Vol. 5 1993, Chlorine Oxygen Acids and Salts, Kaczur, J. and Cawlfield, D. Editors, p.191. John Wiley & Sons, Inc) (SCD) is actually a misnomer, for there is nothing stable about molecular chlorine dioxide ($ClO_2$). SCD is actually a solution of sodium chlorite ($NaClO_2$) which has a peroxy compound added which reduces $ClO_2$ back to $NaClO_2$, whereby a stabilized source for $ClO_2$ is achieved. Depending on the concentration of $NaClO_2$, some $ClO_2$ is present. For example a 2000 mg/L concentration would have much less than 2 mg/L of $ClO_2$—there is some but very little. SCD can quickly form significant amounts of $ClO_2$, but only upon acidification with say a protic acid at very low pHs. (SCD) really has no chemical meaning. In practice SCD is synonymous with a solution that contains sodium chlorite buffered to a pH usually greater than pH 8. If the pH of a sodium chlorite solution becomes acidic, chlorine dioxide will be generated. Thus, the term stabilized chlorine dioxide refers to a buffered sodium chlorite solution.

SUMMARY OF THE INVENTION

The present invention provides a method of producing $ClO_2$. The safety and effectiveness of $ClO_2$, with its deodorizing, antimicrobial, biofilm control, and bleaching properties is utilized. Different health and cosmetic products can be developed. Different examples could include products for the treatment of herpes, dandruff, acne, skin rashes (poison ivy), ulcers, bed sores, warts, nail fungus, athletes foot, sunburn and gum disease; and products such as antiseptics, disinfectants, and general deodorants from refrigerator sprays to oral mouthrinses. As an oral mouthrinse alone, it could be used as a breath freshner, periodontal irrigant, and dental rinse/whitener maintenance.

It is an object of the invention to provide a readily available source of $ClO_2$ that can be used within 30 minutes of admixing two solutions or components.

Another object of the invention is to enable products to have a long shelf life by not only keeping the two solutions/mixtures separate, but by having a stable, long half-life activator.

Another object of the invention is to have a $ClO_2$ solution which is in equilibrium with its reactants at a useful concentration that can be flavored or fragranced to mask the taste or odor of $ClO_2$.

Another object of the invention is to use a non-chlorine/hypochlorite source as the activator—thus preventing the formation of trihalomethanes, which are suspect as health risks.

A final object of the invention is to use a naturally occurring substance which meets the specifications of the "Food Chemicals Codex" and is on the generally reorganized as safe (GRAS) list of the FDA.

DETAILED DESCRIPTION OF THE PREFERRED EMBODIMENT

Generally, the method of the present invention comprises an initiator/activator of an alkali metal iodide, preferably potassium iodide (KI); with a composition containing an alkali metal chlorite, preferably sodium chlorite ($NaClO_2$), in an aqueous or non-aqueous base; along with preferably, an acid, a sweetener, a buffer, an emulsifier, and a flavor or fragrance.

Preferably, the sodium chlorite level is provided in excess, so escaping and/or reacting $ClO_2$ can be replaced. Typically, the sodium chlorite is present in an amount from about 0.01% to about 5% by weight of the composition, and preferably 0.05% –2.75% (500 mg/L–27,500 mg/L).

The KI is present in an amount suitable to interact with the sodium chlorite to form the $ClO_2$. The $ClO_2$ formation terminates in an equilibrium concentration. The concentration achieved will depend on the precise concentration of each of the constituents in the composition. If for example, the total weight of an aqueous solution is to be 480 g, then about 4 g of a 25% sodium chlorite solution would be activated by approximately 0.05 g of KI which is 1.25% (0.05/4) of the weight of the 25% sodium chlorite solution. This is approximately 0.01% KI of the total weight, which is actually within the maximum level allowed as a source of dietary iodine (Chapter 21, Code of Federal Regulations, Part 184.1634(d)).

What is unique and non-obvious about this invention is the role of iodide ion (I—) and chlorite ion. The KI activator reacts with chlorite ion to form an intermediate. When the solution becomes slightly acidic, an equilibrium is established producing a steady state concentration of a second intermediate that can be stored for long periods of time. In the presence of excess chlorite ion, the storable intermediate produces and maintains a relatively constant concentration of chlorine dioxide.

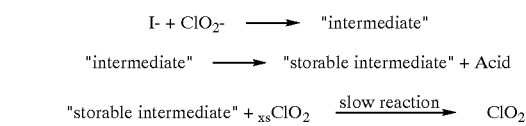

This inventor believes the above reaction is sufficiently disclosed, but the actual chemistry seems to involve a complicated reciprocating reaction. It involves I3— (the tri-iodide ion) as an intermediate. It also involves IO3— (iodate ion) as a very stable intermediate. Thus, the invention could use KIO3 (potassium iodate) in the proper stoichiometric proportion. But due to the greater cost of the halate over the halide, and other complications, KI is prefered. The equations given above in specific chemical terms would read as follows:

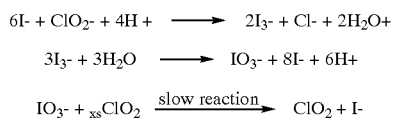

The method encompasses a two part composition. Part 1 of the composition is on the basic side and has a useful concentration of sodium chlorite. One preferred solution of sodium chlorite is sold by Vulcan Chemicals under the name "Technical Sodium Chlorite Solution 31.25". It is unlike "Anthium Dioxide" which is sold by International Dioxide Inc. and contains stabilizing compounds such as peroxy compounds. The preferred one is 31–32 w/v % active sodium chlorite solution having a pH of ~12.8 (without the presence of peroxy compounds). The % active solution is based on the % of solid sodium chlorite added to the solution. The ANSI standard (AWWA Standard for Sodium Chlorite, 1989, American Water Works Association, ANSI/AWWA B303-88.) specifies that solid sodium chlorite shall not contain less than 78% by weight $NaClO_2$. Manufacturer specifications (Gates, D. 1990, Guidance Manual for Rio Linda Generators, Rio Linda Chemical Co., Sacramento, Calif.) typically require delivered liquid sodium chlorite to contain 24.5% to 25.5% chlorite ion for efficient production of chlorine dioxide as measured by sodium thiosulfate titration (Gates, D., The Chlorine Dioxide Handbook, Water Disinfection Series, 1998, W. Cobban, Editor, American Water Works Association, Denver, Colo., ISBN 0-89867-942-7.).

The prior art for using potassium iodide (KI) with respect to chlorine dioxide chemistry is as a reagent to measure (Standard Methods for the Examination of Water and Wastewater, 1992, 18th ed., Edited by A. E. Greenberg, L. Clesceri and A. Eaton. Washington DC: APHA.) the presence of $ClO_2$. The use of (I—) to maintain a small but microbiologically active concentration of dissolved molecular $ClO_2$ is non-obvious to a person having ordinary skill and knowledge of the art. The prior art's sole use of (I—) is to rapidly be oxidized by the available oxyhalogen species and liberate iodine ($I_2$) which is then titrated with standardized sodium thiosulfate or phenylarsine oxide (PAO). There is no suggestion in the prior art for using small amounts and establishing a continuous low-level creation of $ClO_2$, by using small concentrations of KI as the invention does. On the contrary, the prior art for using KI is to react with all available chlorite anion in solution to get quantitative measurements.

Since the Part 1 composition of the invention uses a very much diluted 31%, then the pH is dropped from 12.8 to approximately 9.8. The NaOH in the 31% is converted to NaCl and the pH will further drop over time. Therefore, in one preferred embodiment, disodium phosphate is added to keep the composition buffered at a pH of 9.7 to prevent the premature activation of the sodium chlorite, which occurs near or below pH 7.

Part 2 of the composition is admixed with Part 1 at the time a useful concentration of $ClO_2$ is desired. Part 2 contains a general, or protic acid, preferably phosphoric acid, which has some buffering capacity. In one preferred embodiment, monopotassium phosphate is used to decrease the pH and buffer the final mixture at a pH of about 6.2. This part may also contain an emulsifier for the flavoring, a flavoring, and a sweetener. Different flavors will give more or less activation, i.e. more or less $ClO_2$ from sodium chlorite. For example, cinnamon will increase activation and peppermint will decrease activation. More of the peppermint may be preferred because the cinnamon flavor will form cinnamic acid giving a bitter taste, if e.g. a mouthwash is desired; but may be used if an acne cleanser is the wanted product. In a mouthwash, saccharin is used as the preferable sweetener for its stability and as a sugar substitute. But in an acne cleanser where more $ClO_2$ may be desired, then d-glucose, a reducing sugar, may be used for increased activation. Depending on the amount of constituents in the two parts, different concentrations of $ClO_2$ will be generated, from 1 mg/L–200 mg/L.

In one preferred concentration, 1 g of sodium chlorite is dissolved in 480 g of water, and 0.05 g of KI are added. This will yield a concentration of about 5 mg/L $ClO_2$, in less than 30 minutes, and is an optimum concentration of KI for 1 g of sodium chlorite. It has been discovered, that if a slightly lesser or greater concentration of KI is used, there is a decrease in $ClO_2$ concentration at 35 minutes, but yet an equal amount of $ClO_2$ at 24 hours.

If KI is dissolved in water first, and $NaClO_2$ is added second, it takes up to 29% more KI. The preferred method then is to place the KI in an 8 cc "activator" vial and add it say to a 16 oz. "base" bottle of an $NaClO_2$ solution.

Eight different experiments were conducted as follows: Stoppered vials containing 60 cc of deionized water, 0.345 g of a 25% $NaClO_2$ solution (a 0.144% aqueous solution of $NaClO_2$), and 0.012 g of $Na_2HPO_4 \times 7H_2O$ received differing amounts of KI, along with 0.05 g $KH_2PO_4$, and 0.03 g of 0.1N $H_3PO_4$. The resulting buffered solution had a pH of 6.2. The amount of $ClO_2$ generated was measured according to the depth of the resulting green color, and an arbitrary number from 1.4 to 2.0 was assigned, with 2.0 being the most intense color or the most $ClO_2$ generated. The vials were assigned their arbitrary numbers, 30 minutes after adding the KI. See Table I.

TABLE I

| Vial | KI (g) | Arbitrary # |
|------|--------|-------------|
| 1 | 0.0012 | 1.4 |
| 2 | 0.0024 | 1.7 |
| 3 | 0.005 | 1.9 |
| 4 | 0.007 | 1.8 |
| 5 | 0.012 | 2 |
| 6 | 0.018 | 1.8 |
| 7 | 0.026 | 1.5 |
| 8 | 0.037 | 1.4 |

Surprisingly, as seen in the above table, ever increasing amounts of KI did not produce ever increasing amounts of $ClO_2$. Post admixing of KI with $NaClO_2$ solution showed: In Vial #s 1–4 at 3 minutes, no evidence of free iodine (as evidenced by a brown tint). Vial #5 had a brown tint, but cleared at 3 minutes. Vial #6 had a brown tint but cleared at 7 minutes. Vial #7 was light brown at 30 minutes. Vial #8 was brown at 30 minutes.

Vials #2–#6 were more ideal, in that good activation occurred without any objectionable browning after 7 minutes. This is from approximately 20 to 140 (or an average of 80) times as much 25% NaClO2(g) solution as KI(g). The KI is thus 1/80 or 1.25% of the 25% NaClO2 solution by weight.

Thirteen different experiments were conducted as follows: Stoppered vials containing 60 cc of deionized water with 0.012 g of Na2HPO4x7H2O and differing amounts of 25% NaClO2, received 0.00625 g KI, 0.05 g KH2PO4, and 0.025 g 0.1N H3PO4. As in the above experiment, arbitrary numbers were assigned to the color of the solution, with the greater numbers, reflecting the higher ClO2 concentrations. The arbitrary numbers were assigned 30 minutes after adding the KI. See Table II.

TABLE II

| Vial | 25% NaClO$_2$ (g) | COLOR |
|------|-------------------|-------|
| 1    | 0.345             | 1.4   |
| 2    | 0.355             | 1.5   |
| 3    | 0.365             | 1.5   |
| 4    | 0.375             | 1.4   |
| 5    | 0.385             | 1.4   |
| 6    | 0.395             | 1.5   |
| 7    | 0.405             | 1.5   |
| 8    | 0.415             | 1.6   |
| 9    | 0.425             | 1.6   |
| 10   | 0.485             | 1.6   |
| 11   | 0.555             | 1.6   |
| 12   | 0.625             | 1.6   |
| 13   | 0.695             | 1.6   |

As shown from the experiment, using the same KI concentration, and increasing concentrations of a 25% NaClO2 solution above 0.415 g, did not produce increasing amounts of ClO2 by the 30 minute mark. A preferred embodiment of the invention includes 0.485 g of 25% NaClO2, and 0.00625 g of KI per 2 ounces (60 cc) of deionized water which is equivalent to 3.88 g of 25% NaClO2 and 0.05 g KI per 16 ounces. This would be approximately a 0.20% (2000 mg/L) solution of NaClO2.

Therefore, a preferred example would include 467 g of deionized water, 3.88 g of a 25% NaClO2 solution, and 0.096 g of Na2HPO4x7H2O in a 16 oz stock bottle. Separately, an activator could contain 4.8 g deionized water, 0.05 g KI, 0.4 g KH2PO4, 0.2 g of 0.1N H3PO4, and sweetener and flavor as needed or desired in an 8 cc vial.

The bottle and vial are kept separately, and admixed when a useful concentration of ClO2 is desired. The above preferred example has been kept for over one year at 45 degrees Celsius, and when admixed produced a useful concentration of ClO2, which when kept tightly capped remained useful for over three months.

Previous inventions have used solutions of sodium hypochlorite (NaOCl), with its half life of 30 days, as the activator. This not only dictates the necessity of a retail shelf life of less than one year, but does not allow flavorings or fragrances, because the NaOCl like NaClO2, reacts with flavorings and fragrances.

The method according to the present invention can be used in aqueous or non-aqueous solutions, with solid or liquid activators at different concentrations, and at various pH levels, depending on the desired body or substrate surfaces for the ClO2 to act upon. Depending on the desired amount of ClO2, the NaClO2 and KI can be adjusted as needed.

The invention is therefore susceptible to various modifications and alternative forms. A specific example has been described herein in detail. It is understood that the invention is not limited to this example alone, but on the contrary, its broad inventive concept is intended to cover all modifications, equivalents, and alternatives falling within the spirit and scope of the invention.

EXAMPLES

If a thick base is desired—a nonaqueous base of glycerin, or an aqueous base thickened with hydroxyethyl cellulose, may contain the KI; and the pH buffered from say 2.5–4.5, and a solution of NaClO2 could be added thereto. This gel would allow longer intimate contact with the skin, when used as a skin cleanser or antiseptic/disinfectant. To facilitate ClO2 crossing the skin barrier, carriers such as d-limmonene could be added.

If higher concentrations of ClO2 are desired—then a reducing sugar such as glucose or a non-hydroxylated aldehyde such as propionaldehyde, could be added to further increase ClO2 production, as could low pKa acids such as potassium bisulfate.

If a 2.76% NaClO2 antiseptic solution is desired, 3.32 g of the 25% solution (0.83 g of NaClO2) is placed in 30 cc of water along with 0.43 g of KI. The required NaClO2 for this formulation is ~20 times more concentrated than the examples presented in Table I. It is important to note that the required increase in KI concentration to achieve a chlorine dioxide concentration suitable for this application is only about 10 times the example concentration. This is a non-obvious and unique feature of this invention. Because a relatively constant source of stable intermediate is maintained, the kinetics and subsequent rate of chlorine dioxide generation does not require a linear increase or decrease in activator compared to sodium chlorite concentration for the establishment of specific chlorine dioxide concentrations, but still falls within the spirit and scope of the invention.

I claim:

1. A method for generating molecular chlorine dioxide by reacting in a solution an alkali metal chlorite with an alkali metal iodide, wherein said alkali metal chlorite is from about 0.03% to about 5% by weight of said solution and said alkali metal iodide is present in an amount of from about 1.4% to about 43% by weight of the alkali metal chlorite.

2. The method of claim 1 wherein the alkali metal chlorite is present in an amount to maintain the chlorine dioxide at a concentration of about 2–200 mg/L.

3. The method of claim 1 wherein the alkali metal chlorite is NaClO2 and the alkali metal iodide is KI.

4. The method of claim 3 wherein said KI is from about 2.8 to about 20.9% by weight of the NaClO$_2$.

5. The method of claim 3 wherein about 0.345 g to about 0.695 g of a 25% NaClO$_2$ solution is used per every 0.00625 g of KI.

6. The method of claim 3 wherein about 0.415 g to about 0.625 g of a 25% NaClO$_2$ solution is used per every 0.00625 g of the KI.

7. The method of claim 1 further comprising a buffering agent to maintain the reaction pH at about 6.2.

8. The method of claim 7 wherein the buffering agent is selected from the group consisting of phosphoric acid, disodium phosphate and monopotassium phosphate.

9. The method of claim 1 wherein the alkali metal chlorite is sodium chlorite of about 2.5–3.0% by weight of said solution.

10. The method of claim 6 wherein approximately 0.012 g of disodium phosphate and about 0.05 g of monopotassium phosphate are present.

11. A method for generating molecular chlorine dioxide by reacting a sodium chlorite solution with potassium iodide, wherein the sodium chlorite solution is formed by adding 3.32 g of a 25% NaClO$_2$ solution by weight to 30 cc of water and the potassium iodide is in an amount of 0.43 g.

\* \* \* \* \*